United States Patent [19]

Jorgensen

[11] Patent Number: 4,859,964
[45] Date of Patent: Aug. 22, 1989

[54] METHOD AND CIRCUIT FOR AUTOMATIC GAIN CONTROL OF A SIGNAL

[76] Inventor: Poul R. Jorgensen, LaRomantica 8, Almunocar, Apt. 217, Malaga, Spain

[21] Appl. No.: 111,023
[22] PCT Filed: Feb. 3, 1987
[86] PCT No.: PCT/DK87/00010
§ 371 Date: Oct. 9, 1987
§ 102(e) Date: Oct. 9, 1987
[87] PCT Pub. No.: WO87/04877
PCT Pub. Date: Aug. 13, 1987

[30] Foreign Application Priority Data

Feb. 11, 1986 [DK] Denmark .................................. 651/86

[51] Int. Cl.[4] .............................................. H03G 3/20
[52] U.S. Cl. ..................................... 330/279; 330/129
[58] Field of Search ................. 330/129, 132, 278, 279

[56] References Cited

U.S. PATENT DOCUMENTS

| | | | |
|---|---|---|---|
| 4,297,527 | 10/1981 | Pate | 381/107 |
| 4,546,326 | 10/1985 | Van Uffelen et al. | 330/129 |
| 4,553,104 | 11/1985 | Olsen | 330/129 |

Primary Examiner—Steven Mottola
Attorney, Agent, or Firm—Dressler, Goldsmith, Shore, Sutker & Milnamow

[57] ABSTRACT

A system for automatically readjusting the gain of an amplifier so that the dynamic range of an input analog signal does not exceed a predetermined digital word length includes a digitally controlled amplifier. Output of the amplifier is coupled to an analog-to-digital converter. Output of the analog-to-digital converter is coupled to a microprocessor system. A digitized representation of the input signal is stored in the microprocessor system. The microprocessor system then compares amplitude values of the stored digital representation with predetermined upper and lower limit values. A control signal is generated for the amplifier depending on whether or not the maximum values of the stored digital representation fall between the predetermined upper and lower limits. The gain of the amplifier is incrementally adjusted such that the dynamic range of the amplified representation of the input signal does not exceed the predetermined digital word length of the microprocessor system.

8 Claims, 1 Drawing Sheet

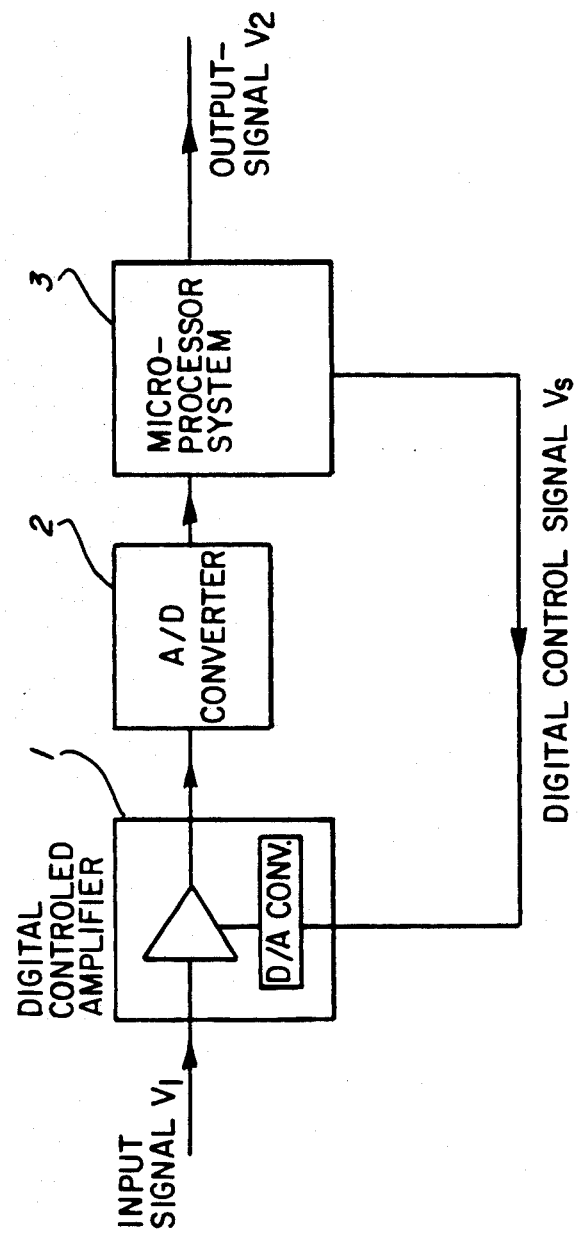

METHOD AND CIRCUIT FOR AUTOMATIC GAIN CONTROL OF A SIGNAL

FIELD OF THE INVENTION

The invention relates to an apparatus and a method for automatic gain control of a signal. More particularly, the apparatus and method relate to adjustment of gain so as to maintain an output signal between upper and lower limits.

BACKGROUND OF THE INVENTION

Known prior art gain control circuits have been implemented exclusively with analog devices, by combining both analog circuits and digital circuits or with only digital electronics. Known prior art gain control circuits detect a single characteristic parameter of the input signal which is to be adjusted. The selected parameter may include the main valve, effective value or peak value of the signal.

Where it is desirable, because of downstream processing, to use a gain control circuit which includes digital elements problems have been encountered in processing analog input signals having large dynamic ranges. The problems arise out of the fact that the digital circuitry, which might be implemented in part as a microprocessor, is usually organized to have a predetermined digital word length.

If the dynamic range of the analog signal is too large, it will at times exceed the predetermined digital word length. When this happens, it is necessary to resort to multiple word arithmetic which can be slower and more complicated than single word arithmetic.

In some applications, the input analog signal to be processed may lie within a relatively narrow, predetermined frequency range and have an overall known wave form the dynamic range of which varies. At times, the signal which is intended to be processed may be distorted due to noise superimposed thereon.

If the amplitude of the noise exceeds that of the signal to be processed, it will have an undesired effect on the operation of the automatic gain control circuitry. Hence, in addition to being able to deal with an input signal of a varying dynamic range, it is also desirable to be able to filter the signal prior to carrying out the gain control-related processing.

SUMMARY OF THE INVENTION

In accordance with the invention, a method of processing any input analog signal having variable values and of automatically adjusting the gain of a corresponding amplifier system is provided. The method includes the steps of amplifying the input signal by a predetermined value of gain.

Subsequent to the amplifying step, the signal is then digitized. The digitized values of the analog signal are then stored.

A determination is then made as to whether or not the digitized values are increasing or decreasing. If the digitized values are increasing, those values are compared to an upper predetermined threshold. If the maximum digital values exceed the predetermined threshold, the gain is subsequently reduced incrementally. If the digitized values are decreasing, they are compared to a predetermined lower threshold. If the maximum digitized values fall below the lower threshold, the gain of the system is subsequently incrementally increased.

In addition, if desired, the digitized values can be filtered so as to remove unwanted components therefrom prior to the determining step. The filtering step can include determining of frequency value for the unwanted component and removing the unwanted component from the digitized values.

A system for processing an input analog signal includes a variable gain amplifier for amplifying the input analog signal by a predetermined gain value. Analog-to-digital converter circuitry is provided for digitizing the amplified analog signal.

A memory is provided for storing the digitized values received from the analog-to-digital converter. Control circuitry is provided for determining if the digitized values are increasing or decreasing.

The control circuitry can also compare the values of the digitized signal to an upper threshold if that signal is increasing. The gain adjusting circuitry is provided for subsequently, incrementally reducing the gain value if a selected digitized maximum value exceeds the upper threshold.

The control circuitry also compares the values of the digitized signal to a lower predetermined threshold if that signal is decreasing. The gain of the amplifier is subsequently, incrementally increased if a maximum digitized value falls below the lower threshold.

In addition, the system can also include circuitry for filtering the digitized values so as to remove unwanted components therefrom.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE DRAWINGS

FIG. 1 is an overall block diagram of a system for automatic gain control of an input analog signal in accordance with the present invention.

DETAILED DESCRIPTION OF THE PREFERRED EMBODIMENTS

While this invention is susceptible of embodiment in many different forms, that is shown in the drawings and will be described herein in detail a specific embodiment thereof with the understanding that the present disclosure is to be considered as an exemplification of the principles of the invention and is not intended to limit the invention to the specific embodiment illustrated.

FIG. 1 is an overall block diagram of an automatic gain control system. As illustrated on the drawing, an analog input signal $V_1$ is supplied to an analog amplifier 1. The gain factor of the amplifier 1 can be adjusted in increments by means of a digital control signal $V_s$ which is supplied to the gain control input of the analog signal amplifier 1.

An amplified analog signal is emitted at the output of the analog amplifier 1 to the input of an analog-to-digital converter 2. The analog-to-digital converter 2 samples the amplified analog signal and produces, at its output, a digital signal representation of the input signal $V_1$ having sampled amplitude values of the amplified analog signal at successive sampling times.

The analog input signal $V_1$ is a signal with a varying signal level which after the amplification in the automatic gain control circuit has to be within predetermined upper and lower limits or thresholds respectively. The upper and lower limits are identified as $G_2$ and $G_1$ respectively. In many instances, the analog input signal lies within a predetermined, narrow frequency range. It will be understood of course that the invention need not be limited to a narrow frequency interval.

The digitized signal representation, or digital values, is supplied to the data input of a known microprocessor system. The digitized signal representation is stored in storage locations in a storage device in the microprocessor 3. The sampling and storage of input signal take place in a so-called measurement period of a duration corresponding to a given number of signal periods. A measurement period is followed by an adjustment period of a preset duration. During the adjustment period, the signal is gain-controlled if necessary, but without sampling and storage of the signal taking place during this period.

The adjustment period is followed by another measurement period in which the signal is sampled and stored again. This measurement period is again followed by an adjustment period, etc. Hence, a measurement period and an adjustment period alternate. This division may, for example, be made by a synchronization signal. It can also be carried out in other suitable ways.

Continuous adjustment of the signal amplitude is thus not implemented as in the case of known prior art automatic gain control units using analog circuit devices where the gain control is implemented depending on e.g., mean value, effective value or peak value of the input signal. In the system of FIG. 1, the gain adjustment is limited to preset adjustment periods.

During a measurement period, the microprocessor system 3 processes the digital signal representation stored in the storage device in accordance with a stored control program and supplies to the amplifier 1, during a subsequent adjustment period a digital control signal $V_s$. The control signal $V_s$ need not be supplied during the adjustment period following immediately after the measurement period. Instead it may be supplied in an arbitrary adjustment period following the measurement period to the gain control input of the digitally controlled amplifier in accordance with this program. The digital control signal $V_s$ controls the gain of the amplifier 1 in increments.

The processing performed by the microprocessor system 3 of the digitized and stored signal may consist of a comparison of the digital signal representation stored in the storage device with a predetermined upper limit value $G_2$ and a predetermined lower limit value $G_1$ respectively coded into the microprocessor system 3. Both of these limit values being referred to the signal input.

If the microprocessor system 3 ascertains during the measurement period that the signal level of the signal is increasing, the amplitude values of the stored digital signal representation are compared to the upper limit value $G_2$. If the highest value of the digitized values exceeds the upper limit value $G_2$, the microprocessor system 3 emits a digital control signal $V_s$ to the gain control input of the digitally controlled amplifier 1.

The value of $V_s$ is such that the gain is adjusted (in increments) in a direction which attenuates the signal $V_2$. This stepwise adjustment of the gain of the amplifier 1 continues until the highest amplitude value of the digitized signal is lower than $G_2$.

If during the measurement period, the microprocessor system 3 ascertains that the signal level of the digitized signal is decreasing, the amplitude values of the stored digital signal representation are compared to the lower limit value $G_1$. If the highest value of the digitized amplitude values comes below the lower limit value $G_1$, the microprocessor device 3 emits a digital control signal $V_s$ to the gain control input of the digitally controlled amplifier 1.

The value of $V_s$ is such that the gain is adjusted in increments in a direction which amplifies the signal $V_2$. This stepwise adjustment of the gain of the amplifier 1 continues until the upper amplitude of the digitized signal is above $G_1$.

An adjustment of the gain of the amplifier 1 is implemented either if the highest amplitude value of an increasing signal level exceeds the upper limit value $G_2$, or if the highest amplitude value of a decreasing signal level comes below the lower limit value $G_1$. For example, if the highest amplitude value of a decreasing signal level comes below the upper limit value $G_2$, no adjustment takes place.

As a result of the method and apparatus described in the foregoing, the highest amplitude value of the adjusted signal (output signal $V_2$) will always be between the lower limit value $G_1$ and the upper limit value $G_2$. Thus, the dynamic range of the signal can always be adapted to a predetermined digital word length so that it does not cause overload or create any other irregular operation in any subsequent processing circuit.

The adjusted output signal $V_2$ can also be used internally for other purposes, e.g., as a control signal. As the gain of the digitally controlled amplifer 1 is adjusted in increments during the adjustment periods, any distortion of the output signal $V_2$ in connection with the adjustment is limited to these periods which are already known.

The processing performed by the microprocessor system 3 on the stored digitized signal may also include a computation of the frequency of the input signal $V_1$. A subsequent adjustment on the basis of this frequency value may be carried out as explained below. If, for example, an undesired signal (an interference signal) occurs which is superimposed on the desired input signal, and if the amplitude of that interference signal is higher than the amplitude of the desired input signal, then the undesired signal will reduce the sensitivity of the automatic gain control system because the amplitude of the undesired signal is higher than that of the desired input signal. As a result, the adjustment takes place in response to the higher amplitude of this undesired signal.

This problem can be avoided if the control program of the microprocessor system 3 analyzes, during the measurement period, the digital signal representation of the total signal—i.e., both the undesired signal and the desired signal—stored in the storage locations of the storage device. On the basis of a prior determination of the frequency of the desired input signal obtained as described above, the microprocessor system 3 determines the frequency of the undesired signal. If this frequency differs from that of the desired input signal, then the microprocessor system deletes or erases the storage locations of the undesired signal in the storage device, whereupon the adjustment of the input signal will take place in the above-described fashion. Hence, a reduction of the automatic gain control sensitivity is avoided as a result of a large interference signal.

This mode of adjustment can be developed so that the adjustment takes place dependent, e.g., on both amplitude, frequency and phase, i.e., depending on arbitrarily complicated functions of the input signal.

Even if it is not shown on the drawing, the synchronization signals required for operation of the circuit as well as power and voltage levels are supplied to each individual circuit device of the automatic gain control circuit of FIG. 1.

From the foregoing, it will be observed that numerous variations and modifications may be effected without departing from the spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

I claim:

1. A method of processing an input analog signal having varying values and of automatically, incrementally adjusting the gain of an amplifier system comprising:
   amplifying the analog signal by a predetermined gain value;
   digitizing amplified values of the analog signal;
   storing the digitized values of the analog signal;
   determining if the digitized values are increasing or decreasing;
   comparing the digitized values to an upper, predetermined threshold if those values are increasing and subsequently, incrementally decrease the gain value if a selected maximum digital value exceeds that upper threshold;
   comparing the digitized values to a lower, predetermined threshold if those values are decreasing; and
   subsequently, incrementally increasing the gain value if a selected maximum digitized value falls below that lower threshold.

2. A method as in claim 1 including:
   processing the digitized signal so as to remove unwanted components therefrom.

3. A method as in claim 2 wherein the processing step includes:
   determining a frequency of a selected component of the digitized signal;
   determining a frequency of the unwanted component;
   deleting from the digitized signal the unwanted component.

4. A method of processing a varying input analog signal and of automatically, incrementally adjusting the gain of an amplifier system comprising:
   amplifying the analog signal by a predetermined gain value;
   digitizing the amplified values of analog signal;
   storing the digitized values;
   processing the digitized values so as to remove unwanted components therefrom;
   comparing the remaining digitized values to an upper, predetermined threshold and subsequently, incrementally reducing the gain value if a selected maximum value exceeds that upper threshold; and
   comparing the remaining digitized values to a lower, predetermined threshold and subsequently, incrementally increasing the gain value if a selected maximum value falls below that lower threshold.

5. A system for processing a varying analog signal comprising:
   means for amplifying the analog signal by a predetermined gain value;
   means for digitizing the amplified signal;
   means for storing digitized values;
   means for determining if the digitized values are increasing or decreasing;
   means for comparing the values of the digitized signal to an upper threshold if that signal is increasing including means for subsequently step-wise reducing the gain value if a selected maximum value exceeds that upper threshold; and
   means for comparing the values of the digitized signal to a lower, predetermined threshold if that signal is decreasing including means for subsequently step-wise increasing the gain value if a selected maximum value falls below that lower threshold.

6. A system as in claim 5 including:
   means for processing the digitized signal so as to remove unwanted components therefrom.

7. A system as in claim 6 wherein said processing means includes:
   means for determining a frequency of a selected component of the digitized signal;
   means for determining a frequency of the unwanted component; and
   means for deleting from the digitized signal the unwanted component.

8. A system for processing an input analog signal and for automatically adjusting the amplification thereof in increments comprising;
   means for amplifying the analog signal by a predetermined gain value;
   means for digitizing the amplified signal;
   means for processing the digitized values so as to remove unwanted components therefrom;
   means for comparing the values of the remaining digitized signal to an upper threshold including means for subsequently, incrementally reducing the gain value if a maximum value exceeds that upper threshold; and
   means for comparing the values of the remaining digitized signal to a lower, predetermined threshold including means for subsequently, incrementally increasing the gain value if a selected maximum value falls below that lower threshold.

* * * * *